United States Patent
Consolaro et al.

(10) Patent No.: US 8,871,137 B2
(45) Date of Patent: Oct. 28, 2014

(54) PROCESS FOR PRODUCING MEDICAL INSTRUMENTS

(75) Inventors: Roberto Consolaro, Arzignano (IT); Rajeev Kabbur, Montebello Vicentino (IT)

(73) Assignee: Brevetti Angela S.r.l., Arzignano (VI) (IT)

( * ) Notice: Subject to any disclaimer, the term of this patent is extended or adjusted under 35 U.S.C. 154(b) by 186 days.

(21) Appl. No.: 13/261,074

(22) PCT Filed: Jun. 10, 2010

(86) PCT No.: PCT/IT2010/000259
§ 371 (c)(1), (2), (4) Date: Mar. 21, 2012

(87) PCT Pub. No.: WO2010/143219
PCT Pub. Date: Dec. 16, 2010

(65) Prior Publication Data
US 2012/0179107 A1 Jul. 12, 2012

(30) Foreign Application Priority Data
Jun. 11, 2009 (IT) ................ VI2009A0138

(51) Int. Cl.
*B29C 49/32* (2006.01)
*B29C 49/76* (2006.01)
*A61M 5/31* (2006.01)
*B29L 31/00* (2006.01)
*B29C 49/04* (2006.01)

(52) U.S. Cl.
CPC ........... *B29C 49/76* (2013.01); *B29L 2031/753* (2013.01); *B29C 2791/007* (2013.01); *B29C 2791/001* (2013.01); *A61M 5/3129* (2013.01); *B29L 2031/7544* (2013.01); *B29C 49/04* (2013.01); *B29C 2791/006* (2013.01); *A61M 2005/3131* (2013.01)
USPC .................... 264/531; 264/523; 264/540

(58) Field of Classification Search
None
See application file for complete search history.

(56) References Cited

U.S. PATENT DOCUMENTS
2005/0121034 A1    6/2005   Kennedy

FOREIGN PATENT DOCUMENTS
WO    WO 2007/007178    1/2007
WO    WO 2007/083518    7/2007

OTHER PUBLICATIONS
International Search Report dated Jun. 8, 2011.

*Primary Examiner* — Monica Huson
(74) *Attorney, Agent, or Firm* — Hedman & Costigan, P.C.; James V. Costigan; Kathleen A. Costigan

(57) ABSTRACT

A process for producing medical instruments (7) comprising the operations of extruding plastic material in order to obtain a heated tubular element (1) made of molten state plastic material, performing on the tubular element (1) a blow molding in order to obtain a plurality of medical containers (6). The process comprises the operation of calibrating the inner surface (6a) of the various medical containers (6), performed after the operation of extruding plastic material, in order to make smooth and continuous the inner surface (6a) of each of the medical containers (6).

10 Claims, 3 Drawing Sheets

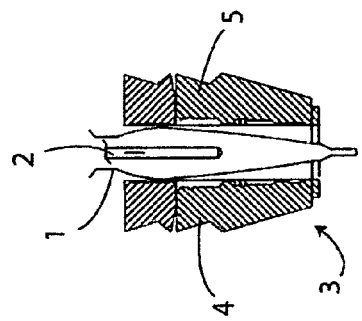
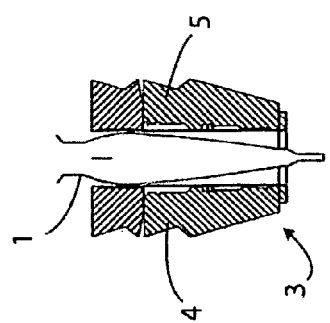
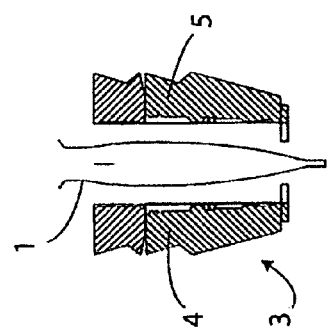
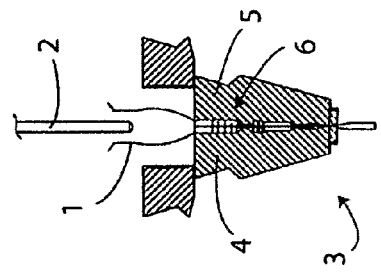
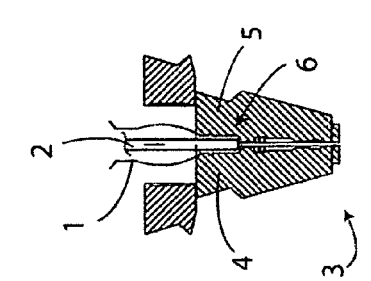
Fig. 1
Fig. 2
Fig. 3
Fig. 4
Fig. 5
Fig. 6

PROCESS FOR PRODUCING MEDICAL INSTRUMENTS

The present invention concerns a process for producing medical instruments intended to contain a medical liquid to be injected or an organic liquid to be sampled from organisms.

The invention that it is going to be herewith described also refers to a medical instrument, such as a syringe for injections, obtained through the aforesaid process.

As known, medical and pharmaceutical instruments of modern design, such as containers, bottles, vials, hollow cylindrical bodies for the sliding of pistons in syringes and so on, are mostly made of plastic material through advanced injection moulding processes, on one hand, and extrusion and blow moulding and the other hand.

Each of the two production technologies mentioned above presents special prerogatives and features, by virtue of which the producers base their constructive choices.

The present invention is directed specifically to the second of these technologies, i.e. the extrusion and blow moulding, widely adopted for the high reliability that allows to get, in a tightly controlled environment, aseptic medical products designed to contain solutions.

In particular, the technology of extrusion and blow moulding is used in the pharmaceutical industry to produce highly sterilized medical containers, suitable to receive inside of them directly or indirectly, at a later stage, liquids or solutions of various kind limiting their degree of decay and/or contamination.

The medical containers obtained through extrusion of plastic material and blow moulding thus lend themselves to contain pharmaceutical parenteral solutions intended to be injected into deep tissues by means of syringes, drip-feeds or other instrument, eyes drops, antibiotics, dialysis, blood infiltration solutions and so on.

Shape and size of the medical containers produced by the technology in question depend on the requests expressed from time to time by the market.

In any case, the technology of extrusion and blow moulding which produces medical instruments including containers takes place with the aid of a forming dye made of two pieces or half shells facing and opposite each other.

The process includes firstly the extrusion of plastic granules into the forming dye kept opened, creating a hollow heated tube made of malleable plastic material, at the molten state, better known as "parison" in the technical jargon of the field of relevance herewith.

The production process continues with the closing of the "parison" between the half shells of the forming dye and, in such conditions of closed forming dye, the subsequent blow moulding of one or more medical containers in their definitive and final shape, by blowing compressed air and/or suction creating vacuum.

More specifically, the aforesaid process produces a unique medical container where the forming dye presents only one cavity, for example in case containers of a certain size are needed to be produced.

The closure of the forming dye onto the parison produces several medical plastic containers aligned each other when the forming dye presents a plurality of cavities (so-called multi-cavity): this typically occurs when medical containers of smaller size are needed to be produced.

When the parison is closed by a multi-cavity forming dye with the goal of creating several medical containers through a single blow moulding operation, at the junction or separation edge of two medical containers adjacent or contiguous each other, the side wall of the respective medical containers, both internally and externally, is inevitably uneven and irregular, or at least not perfectly smooth.

This technical result, while on one side does not represent a particular drawback where the medical containers are intended to the simple containment of liquids, on the other side constitutes a rather serious and cumbersome limitation where the containers themselves are intended to receive a movable insert, e.g. the piston of a syringe, for pushing and/or sucking liquids, organic substances and the like.

Indeed, the irregularities present on the surface of the inner side wall of the various medical containers cause problems of insertion of the movable insert but mostly limit the seal between the movable insert and the corresponding medical container into which the movable insert is inserted by precision and slides.

For example, if the medical instrument equipped with the container is represented by a syringe, the coupling between the piston and the inner surface of the container is imprecise and not optimum at the aforesaid manufacturing defect of the container.

It follows that even a minimal amount of air or any liquid contained in the medical containers flows between the two zones physically separated by the piston, with the obvious and well-known disadvantages that this entails.

The present invention aims to overcome the drawbacks of the known art mentioned above.

In particular, main purpose of the invention is to develop a process for the production of medical instruments based on the technology of plastic material extrusion and subsequent blow moulding into a multi-cavity forming dye which allows to make the inner surface of the medical containers more suitable than the equivalent known technique to effectively cooperate with a relative movable insert which is introduced inside the medical container and can be operated by the operator in order to perform a medical treatment on a body.

In other words, primary purpose of the present invention is to implement a process for the production of medical instruments which improves the seal between a movable insert and the inner surface of a medical container, obtained by blow moulding in a multi-cavity forming dye, into which said movable insert is inserted and made sliding by actuating means.

Within such a purpose, it is task of the present invention to provide a process for the production of medical instruments which makes more effective and safer than the known art the medical treatments carried out through medical instruments manufactured by extrusion of plastic material and blow moulding in a forming dye having usually a plurality of cavities aligned one with another.

It is a further purpose of the present invention to conceive a process for the production of medical instruments which can be actuated through the techniques and machines nowadays available on the market to manufacture medical instruments through the process of extrusion of plastic material and blow moulding.

The aforesaid purposes are achieved through a process for producing medical instruments according to the attached claim 1, to which they refer for brevity.

Additional application features of detail of the process of the invention are set forth in the corresponding dependent claims.

Advantageously, the process of the invention allows to produce, by extrusion of plastic material and blow moulding into a multi-cavity forming dye, medical instruments comprising a medical use container having a high degree of sterility and provided with a inner surface perfectly smooth, continuous and regular.

Each container of the medical instrument obtained through the process of the invention is thus extremely suitable for an insert which is made sliding inside the container itself by actuating means, such as the hand of an operator, in order to perform a medical-health treatment on a human body or an organism.

In the invention, in fact, the coupling between the movable insert and the inner surface of the relative medical container is marked with an almost optimal precision which determines between the aforesaid components (container and insert) a watertight, unlike what can be checked in commercially yet existing medical instruments obtained by extrusion and blow moulding.

Still advantageously, the operation of calibration of the inner surface of the various medical containers is performed continuously with the formation of the containers themselves, while the plastic material is still hot and at the semisolid state.

This involves minimal or almost non-existing variations in the timing of production of the medical instruments and, simultaneously, very effective operating results.

Equally advantageously, the process according to the invention can be implemented using the technologies and machines nowadays in use in the field in order to produce medical instruments by extrusion of plastic material and subsequent blow moulding.

Said purposes and advantages, as well as others that will be better highlighted below, will appear to a greater extent by the following description relating to a preferred application embodiment of the process and a preferred executive embodiment of the medical instrument of the invention, given by illustrative, but not be limited, way with reference to the attached drawings in which:

FIGS. 1-6 are simplified schematic views of the sequential operations of the process of the invention;

Figure 6A:
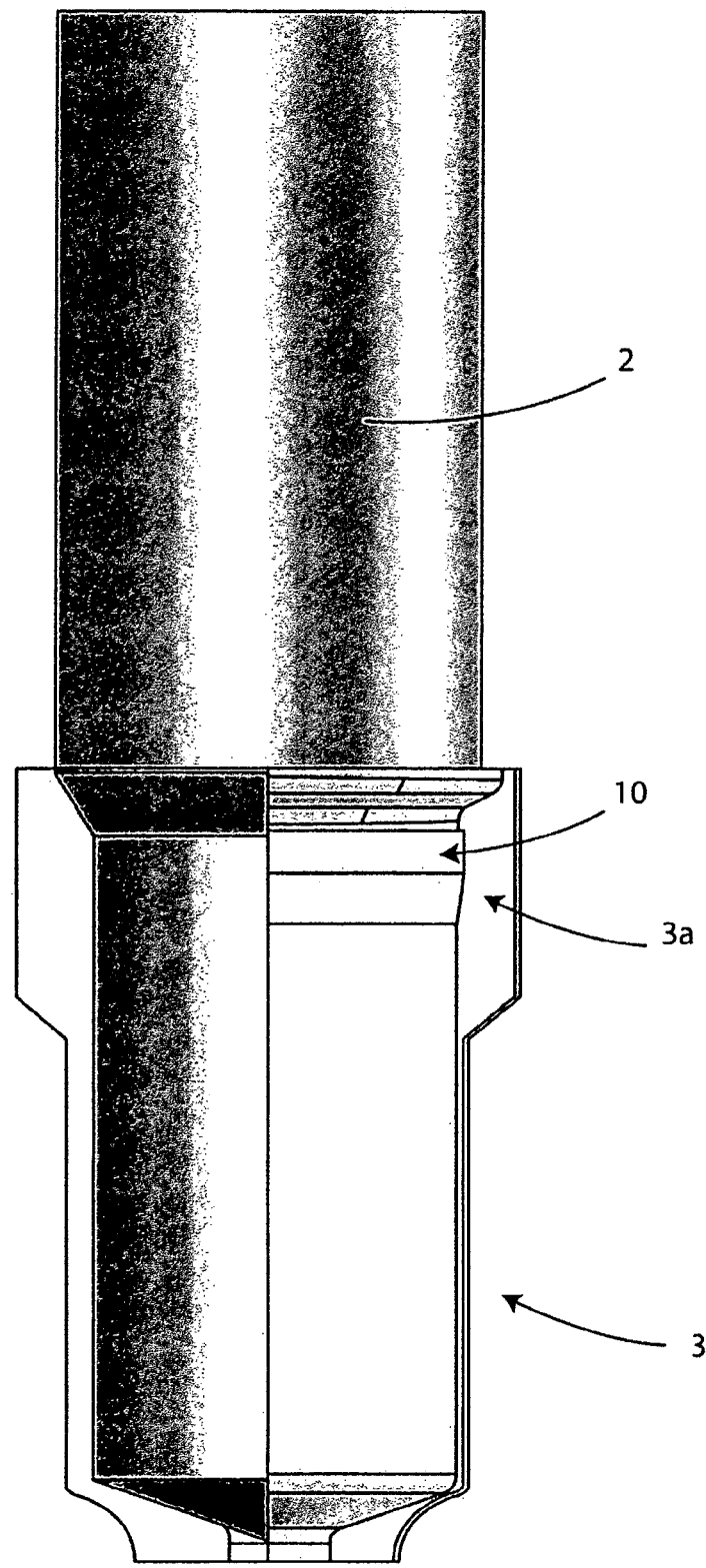
FIG. 6a is an enlargement of an operative phase of the process of FIGS. 1-6.

The process of extrusion and blow moulding of plastic material for the production of medical instruments of the invention is shown in schematic manner in the figures from 1 to 6.

Such a process includes the following operations:
extruding plastic material in order to obtain a heated tubular element 1 made of at least partially molten state plastic material (also known as "parison"), operation depicted in FIG. 1;
performing on such a tubular element a blow moulding in order to obtain a plurality of medical containers 6, each of which generally provided with a neck or a partial shrinkage through which the passage of liquids or organic substances takes place; this operation is outlined in FIG. 4.

In accordance with the invention, the process includes the operation of calibrating the entire inner surface 6a of the medical container 6 (see FIGS. 3 and 4), performed after the operation of extruding the plastic material, suitable to make smooth, regular and continues the inner surface 6a of each of the medical containers 6.

Therefore, the operation of calibrating occurs advantageously while the tubular element 1 is still heated and at least partially at the molten and/or malleable state, and the various medical containers 6 are not yet completely and finally formed.

In a preferred way, the process of the invention comprises the operation of coupling within each of the medical containers 6 a movable insert, for example a piston belonging to a stem or plunger, which is made sliding by actuating means, such as for example the hand of an operator, within the medical container 6 during the execution of a medical-health treatment with such medical instruments.

Then, in case the movable insert is a piston belonging to a plunger, the medical instruments obtained through the process of the invention can be constituted by syringes for injections or samples.

In particular, the calibration operation comprises in the order the following operations:
introducing a plurality of shaped tools 2 inside the extruded tubular element 1, performed after the extrusion of the tubular element 1 itself, according to what illustrated in FIG. 3;
pressing the tubular element 1 onto the shaped tools 2, performed immediately before the operation of blow moulding, according to what shown in FIG. 4.

If the medical instruments consist of syringes, each of the shaped tools 2 includes a cylindrical body having a mainly longitudinal development and the inner surface 6a of the medical container 6 presents a substantially and predominantly linear profile.

As it can be seen in the attached FIGS. 1-6, the operation of extrusion and the operation of blow moulding takes place inside a forming dye 3 of the type in itself known in the field.

The forming dye 3 preferably but not exclusively presents a series of cavities, not shown in the attached figures, each of which having the outer profile which reproduces the prefixed and desired shape for the respective medical container 6.

More specifically, the forming dye 3 is composed of two half shells 4, 5 facing and opposite each other.

The forming dye 3 is open both during the extrusion operation, keeping the half shells 4, 5 spaced apart from the tubular element 1, and during the operation of introducing the shaped tools 2 into the tubular element 1, only bringing near one to another the half shells 4, 5 and placing them close to the tubular element 1 itself, as it is noted from FIGS. 1 and 2.

The operation of pressing the tubular element 1 onto the shaped tools 2, therefore, consists in the operation of closing the forming dye 3 which arranges the half shells 4, 5, one close to the other interposing the tubular element 1 and the shaped tools 2 in this case for the entire longitudinal stretch of the half shells 4, 5.

The process of the invention also comprises the operation of drawing back the shaped tools 2 from the medical containers 6, practically performed after having obtained the medical containers 6 through the aforesaid blow moulding operation.

Preferably but not necessarily, the operation of drawing back the shaped tools 2 occurs while partially opening the forming dye 3, removing one from another the half shells 4, 5 of a predefined distance, e.g. a few tenths of millimeter, reducing the clamping force thereof: this operation is visible in FIG. 5.

In other applications of the process of the invention, not accompanied by reference designs, the operation of drawing back the shaped tools can occur while keeping closed the forming dye.

In a preferred but not binding manner, the process of the invention comprises the operation of retaining inside the forming dye 3 the medical containers 6 just fully formed, performed after the operation of blow moulding and during the operation of drawing back the shaped tools 2 from the related medical containers 6.

Such an operative trick prevents the shaped tools 2, during the backing movement from the respective medical containers 6, dragging disadvantageously with them the containers 6 themselves, thus averting to compromise the structural integrity of the latter.

As it can be seen in FIG. 6a, such an operation of retaining the various medical containers 6 preferably occurs through an annular rebate undercut 10 made in the inner surface of the end 3a of the forming dye 3.

It is understood that in further applicative variants of the process of the invention, the retention of the medical containers can be made through only one rebate undercut or several undercuts separated and distinct each other.

In addition, other applicative solutions of the process of the invention may provide that the operation of retaining the medical containers just formed by blow moulding occurs through other alternative operating tricks or systems and devices.

Advantageously, the operation of blow moulding of the medical containers 6 is performed through the shaped tools 2.

In fact, each shaped tool 2 is provided with a nozzle, not shown, which, besides being used for calibrating the inner surface 6a of the medical container 6, is also used to blow air and carry out in practice the blow moulding of the related medical container 6.

Beyond to calibrating the inner surface 6a of the medical container 6, the shaped tool 2 allows thus to obtain another advantage of considerable relevance with respect to the current state of the art.

Indeed, in performing the calibration of the inner surface 6a, the shaped tools 2 also cool down the plastic material and, most importantly, the same inner surface 6a of the medical containers 6 under formation.

In such a way, the process of the invention creates more rapidly than the known art the ideal conditions of absence or at least maximum reduction of the risks of biological contamination for the product being received into the medical containers 6.

If it is considered that the medical containers are often filled with thermolabile chemical or biological products, highly sensitive to heat up to the point of losing their qualities, the advantages brought by the present invention is immediately evident.

For these products, therefore, the invention reduces the waiting time for introducing the liquid product into the medical container, with the obvious advantages that this implies in terms of productive efficiency.

As already mentioned, object of the present invention is also a medical instrument obtained through the process just described.

Figure 7:
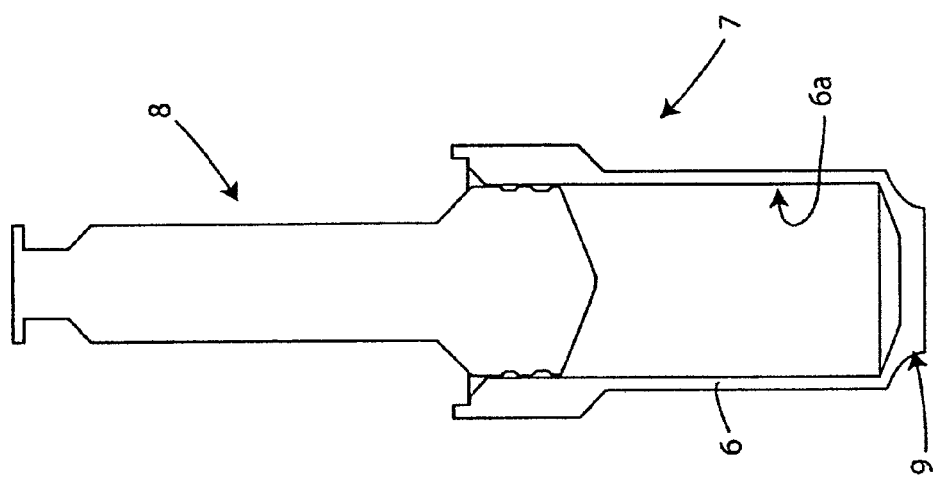
FIG. 7 is a simplified longitudinal section view of the medical instrument of the invention.

As shown in FIG. 7, the medical instrument 7 comprises a medical container 6 obtained by extrusion of plastic material and subsequent blow moulding.

Figure 8:
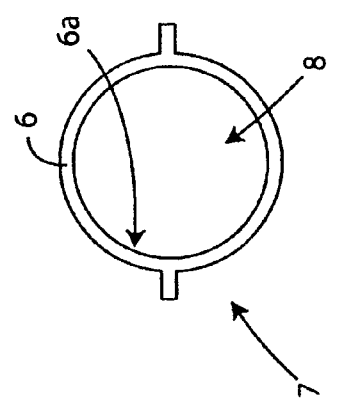
FIG. 8 is a plan view of FIG. 7.

According to the invention, the inner surface 6a of the medical container 6 is smooth and continues in order to provide a constantly hermetic seal with a movable insert 8, visible in FIGS. 7 and 8, introduced into the medical container 6 within which is made sliding by actuating means, not shown for the sake of exposition simplicity, while performing a medical-health treatment with the medical instrument 7.

In the specific case and preferably, the medical container 6 is provided with a neck or shrinkage 9 through which the passage of a liquid, a liquid and not solution from or to the inside of the medical container 6 takes place.

In particular, at the neck 9 the medical instrument 7 may include a needle, not shown, incorporated, using a known technology, in a support element (or needle-support) which forms a single body with the neck 9 of the medical container 6.

On the basis of what exposed above, it is understood, therefore, that the process for the production of medical instruments and the medical instrument obtained through such a process, both object of the current invention being linked by the same general inventive concept, reach the purposes and achieve the advantages already mentioned.

In particular, the operation of calibrating the inner surface of one or more of the medical containers performed during or immediately after their formation in the multi-cavity mould makes perfectly regular and smooth the inner surface itself and, thereby, suitable to allow the correct and effective sliding of a movable insert within the container itself.

In execution, changes will be made to the process of the invention consisting, for example, in an operation of calibrating the inner surface of the medical containers performed with shaped tools which differ from those ones previously described and illustrated only partly in the attached drawings, which does not affect the advantages brought by the present invention.

In addition, other applicative variants of the process of the invention may exist in which the operation of calibration affects only a section of the inner surface of the medical containers.

Moreover, other applications of the process of the invention may provide that the operation of calibrating at least one section of the inner surface is performed only on some of the medical containers under formation.

It is précised that the medical instrument obtained with the process of the invention may not necessarily be formed by a syringe but any element of medical use comprising at least a medical container suitable to receive inside for its normal use a sliding, non static, insert suitable to perform a moving operation of the product contained into the medical container itself. It is clear that several other variants can be made to the process and medical instrument in exam, without for this reason going out of the novelty principle inherent to the inventive idea here expressed, as it is clear that, in the practical implementation of the invention, materials, shapes and sizes of the illustrated details can be any, depending on the requirements, and replaced with others technically equivalent.

Where the constructive features and techniques mentioned in the following claims are followed by reference numbers or signs, those reference signs have been introduced with the sole objective of increasing the intelligibility of the claims themselves and therefore they have no limiting effect on the interpretation of each element identified, by way of example only, by these reference signs.

The invention claimed is:

1. Process for producing syringes (7) comprising the following operations:

extruding plastic material in order to obtain a heated tubular element (1) made of at least partially molten state plastic material;

performing on said heated tubular element (1) a blow moulding operation in order to obtain a plurality of medical containers (6) having a prefixed shape;

calibrating the complete inner surface (6a) of at least one of said medical containers (6), in a calibrating operation performed after said operation of extruding said plastic material, suitable to make smooth and continuous said inner surface (6a) of said medical containers (6) wherein said calibrating operation includes the following operations:

introducing one or more shaped tools (2) into said heated tubular element (1), performed after said extruding of said tubular element (1);

pressing said tubular element (1) onto said shaped tools (2), performed before said blow moulding operation;

wherein said extruding operation and said blow moulding operation occur within a forming mould (3) having a plurality of cavities each of which having a profile which produces the prefixed shape for each of said medical containers (6), said forming mould (3) being composed of two half-shells (4, 5) facing and opposite each other.

2. Process as defined in claim 1 characterized in that it comprises the operation of coupling within each of said medical containers (6) a movable insert (8) that is suitable for sliding by actuator means within said medical container (6) while executing a medical-sanitary treatment on said syringe (7).

3. Process as defined in claim 1 characterized in that said calibrating operation takes place while said tubular element (1) is still heated and in at least a partially molten and/or malleable state.

4. Process as defined in claim 1 characterized in that said forming mould (3) is open during said extruding operation, keeping said half shells (4, 5) spaced apart from said tubular element (1), both during said introducing operation of said shaped tools (2) into said tubular element (1), bringing near one to another said half shells (4, 5) and placing them close to said tubular element (1).

5. Process as defined in claim 1 characterized in that said pressing of said tubular element (1) on said shaped tools (2) consists of the operation of closing said forming mould (3) which arranges said half shells (4, 5) one close to the other interposing said tubular element (1) and said shaped tools (2) for at least one longitudinal stretch of said half shells (4, 5).

6. Process as defined in claim 1 characterized in that it comprises the operation of drawing back said shaped tools (2) from said medical containers (6), performed after having obtained said medical containers (6) through said blow moulding operation.

7. Process as defined in claim 6 characterized in that said drawing back operation of said shaped tools occurs while keeping close said forming mould closed.

8. Process as defined in claim 6 characterized in that said drawing back operation of said shaped tools (2) occurs while partially opening said forming mould (3).

9. Process as defined in claim 6 characterized in that it includes the operation of retaining within said forming mould (3) said medical containers (6) after said blow moulding operation and during said drawing back operation of said shaped tools (2) from said medical containers (6).

10. Process as defined in claim 1 characterized in that said blow moulding operation is performed through said shaped tools (2).

\* \* \* \* \*